United States Patent [19]

McLaughlin

[11] Patent Number: 4,941,990

[45] Date of Patent: Jul. 17, 1990

[54] SKIN CLEANSING-CREAM CONDITIONING BAR

[76] Inventor: James H. McLaughlin, 7 Widgeon La., Little Compton, R.I. 02837

[21] Appl. No.: 424,301

[22] PCT Filed: Feb. 22, 1989

[86] PCT No.: PCT/US89/00788

§ 371 Date: Apr. 7, 1989

§ 102(e) Date: Apr. 7, 1989

[87] PCT Pub. No.: WO89/08444

PCT Pub. Date: Sep. 21, 1989

Related U.S. Application Data

[63] Continuation-in-part of Ser. No. 166,330, Mar. 10, 1988, Pat. No. 4,808,322.

[51] Int. Cl.[5] ......................... A61K 7/48; A61K 7/50; C11D 9/48; C11D 10/04

[52] U.S. Cl. .................................. 252/121; 252/89.1; 252/132; 252/134; 252/174; 252/DIG. 5; 252/DIG. 16; 424/70; 514/846

[58] Field of Search ............... 252/108, 117, 118, 121, 252/122, 132, 134, 174, DIG. 5, DIG. 16, 89.1; 424/70; 514/846

[56] References Cited

U.S. PATENT DOCUMENTS

| | | | |
|---|---|---|---|
| 2,894,912 | 7/1959 | Geitz | 252/121 |
| 3,179,596 | 4/1965 | Farrar | 252/125 |
| 3,376,229 | 4/1968 | Haass | 252/117 |
| 3,814,698 | 6/1974 | Ferrara | 252/370 |
| 3,829,563 | 8/1974 | Barry | 424/70 |
| 3,879,309 | 4/1975 | Gatti | 252/117 |
| 3,951,842 | 4/1976 | Prince | 252/117 |
| 3,991,001 | 11/1976 | Srinivasan | 252/117 |
| 4,007,125 | 2/1977 | Prince | 252/117 |
| 4,012,341 | 3/1977 | Orshitzer | 252/548 |
| 4,026,825 | 5/1977 | Steen | 252/547 |
| 4,046,717 | 9/1977 | Johnston | 252/546 |
| 4,100,097 | 7/1978 | O'Roark | 252/145 |
| 4,198,311 | 4/1980 | France | 252/117 |
| 4,310,433 | 1/1982 | Stiros | 252/132 |
| 4,335,025 | 6/1982 | Barker | 252/550 |
| 4,529,605 | 7/1985 | Lynch | 514/552 |
| 4,582,626 | 4/1986 | Ferrara | 252/122 |
| 4,673,525 | 6/1987 | Small | 252/132 |
| 4,765,922 | 8/1988 | Contamin | 252/90 |

OTHER PUBLICATIONS

Morshauser, F., PCT International Publication No. WO 80/02154, Oct. 16, 1980.

*Primary Examiner*—Dennis Albrecht
*Attorney, Agent, or Firm*—Michael N. Meller

[57] ABSTRACT

An improved skin cleansing-conditioning bar consisting essentially of, by weight, 8% to 38% of an anionic surfactant material selected from the group consisting of a sodium or potassium salt of a C-12–C-18 saturated monocarboxylic acid, a water-soluble, non-soap, anionic detergent selected from the group consisting of sodium and potassium salts higher acyl isethionates, higher alkyl sulfates, higher alkyl sulfonates, higher alkyl monoglyceride sulfates, higher alkylbenzene sulfonates, higher alkyl ethenoxy ether sulfates and mixtures thereof and mixtures of said monocarboxylic acid salt and said anionic detergent in a weight ratio of said monocarboxylic acid salt to said detergent of 18:1 to about 2.5:1; about 12% to 72% of a water-insoluble emollient selected from the group consisting of a C-14–C-18 alkanol and mixtures of said alkanol with a C-14–C-18 alkanoic acid wherein the weight ratio of alkanol to alkanoic acid is in the range of about 23:1 to about 0.6:1; the weight ratio of emollient material to said surfactant material being from about 10:1 to about 1.3:1; 0% to 60% of a starch-derived filler; and 2% to 12% of water; said bar having a pH in the range of 6 to 9.5 measured as a 1% by weight aqueous solution and yielding a satisfactory volume of a non-foaming, cleansing-conditioning cream of moderate viscosity when the wetted bar is rotated and manipulated between the wetted hands of the user. Included in the invention is the method of cleansing and conditioning the skin comprising the steps of forming a cream by rotating and manipulating the inventive bar between the wetted hands, applying the cream to the skin, massaging the cream into the skin and rinsing the cream-treated skin with water.

27 Claims, No Drawings

SKIN CLEANSING-CREAM CONDITIONING BAR

This application is a continuation-in-part of application Ser. No. 166,330 filed March 10, 1988, now issued as U.S. Pat. No. 4,808,322.

FIELD OF THE INVENTION

The described invention relates to an improvement in compositions for cleansing and conditioning the skin as well as to an improved method of cleansing and conditioning the skin. More specifically, the improvement comprises compositions in bar form which contain a weight ratio of a specific emollient material to a specific surfactant material in excess of about 1.3:1 and which yield a non-foaming skin cleansing and conditioning cream upon being manipulated in the wetted hands of the user. The principal emollient ingredient is a C-14–C-18 alkanol, preferably cetyl alcohol, and the principal anionic surfactant is either a sodium or potassium salt of a saturated C-12–C-18 mono-carboxylic acid, preferably the potassium salt, and/or a sodium or potassium salt of a non-soap, anionic detergent selected from the group consisting of isethionate, sulfate and sulfonate detergents. Additionally, the improvement in the method of cleansing and conditioning the skin comprises the step of forming a non-foaming, skin cleansing and conditioning cream by rotating a wetted bar of the inventive composition between the wetted hands of the user.

BACKGROUND AND PRIOR ART

Conventional soap bars are the most commonly used agents for cleansing and conditioning the skin. However, it is well known that soap tends to remove natural oils from the skin, thus causing roughness and dryness of the skin which is apparent when the fingers are rubbed across the washed and dried skin. Additionally, the person cleansing with soap often perceives a stinging sensation both when the hands are wet with the aqueous soap and after the hands are rinsed with water to remove the soap composition and dried.

Many modifications of the basic soap composition have been formulated in an attempt to avoid the disadvantages of the soap compositions. One approach has been to add a mildness agent to the soap bar such as 10% to 40% by weight of an alkyl-carboxy substituted sulfonate as shown in U.S. Pat. No. 4,260,570 or 0.25% to 25% by weight of a quaternary ammonium salt as shown in U.S. Pat. No. 4,303,54 or at least 10% by weight of an oil emollient, e.g., a mixture of mineral oil, isopropyl myristate and a polyethyleneoxide ingredient, as shown in U.S. Pat. No. 4,582,626 or up to 40% by weight of a clathrate of urea and free fatty acid as shown in U.S. Pat. No. 3,991,001.

A second approach has been to replace a major proportion of soap with a milder synthetic detergent and to include a superfatting ingredient such as stearic acid. For example, each of U.S. Pat. Nos. 2,894,912, 3,376,229 and 3,879,309 relates to acid pH bars which are milder than soap wherein a mixture of a major proportion of an acyl isethionate salt and a minor proportion of soap is employed as the principal surfactant in place of soap. These compositions also contain from 10% to 40% by weight of a C-6–C-18 carboxylic acid as a superfatting agent and as a binder-plasticizer. U.S. Pat. No. 3,951,842 describes an improved acyl isethionate bar of the type disclosed above which includes a mixture of sodium sulfate, sodium chloride and a linoleic dimer diacid salt as an anti-mushing agent. U.S. Pat. No. 4,007,124 also describes a similar improved acyl isethionate-soap bar which contains from 10% to 20% by weight of a C-12–C-14 alkane sulfonate salt as an anti-mushing agent.

A third approach has been to omit soap as an ingredient, thereby forming a non-soap, synthetic detergent bar having an acid pH. British Patent No. 1,570,142 describes a non-soap acyl isethionate bar containing a mixture of C-12–C-22 straight chain alcohol or acid in combination with a hydrogenated triglyceride as a binder. This binder system provides a plastic, but hard composition which cannot be achieved by either of the binder components alone. Another improvement in the non-soap, acyl isethionate detergent bars is disclosed in U.S. Pat. No. 4,100,097 wherein the described bars further include, by weight, 10% to 30% of paraffin, 5% to 15% of powdered starch and 10% to 30% of dextrin. Similarly, U.K. Application GB No. 2,057,486 discloses an acid pH detergent bar comprising 30% to 80% by weight of an acyl isethionate in combination with 20% to 70% by weight of a binder consisting of a C-12–C-22 fatty acid or fatty alcohol and an alkyl amide. Another modification of the acid pH, non-soap, acyl isethionate bars is described in U.S. Pat. No. 4,046,717 wherein 10% to 20% by weight of a lactate salt and at least 10% by weight of a glutamate salt are employed together with the acyl isethionate detergent to provide a moisturizing detergent bar. An alternative to the non-soap, acid pH, acyl isethionate synthetic detergent bars is disclosed in U.S. Pat. No. 4,335,025 wherein a C-8–C-16 alkyl sulfosuccinate detergent is combined with a C-12–C-22 fatty acid or alcohol and water to yield a mild detergent bar.

A fourth approach has been to cleanse the skin with a liquid cleansing composition containing an emollient and a foaming detergent. One such composition is described in U.S. Pat. No. 3,829,563 which discloses a foaming liquid emulsion containing 10% to 70% by weight of petrolatum emulsified in an aqueous anionic detergent medium. An anhydrous liquid bath oil comprising a dispersion of a particulate organic detergent in a liquid emollient is described in U.S. Pat. No. 4,026,825. A clear, superfatted, liquid, cleansing composition comprising 5% to 25% by weight of a mixture of potassium soap and fatty acids is described in U.S. Pat. No. 4,310,433. An alternative bathing oil composition is described in U.S. Pat. No. 4,529,605 which comprises an emulsion of a liquid emollient, e.g., isopropyl myristate, in an aqueous mixture of nonionic detergent and cationic detergent.

The present compositions differ from the described prior art soap, synthetic detergent-soap and synthetic detergent bars and the foaming cleansing lotions in that they are non-foaming and form a cleansing and conditioning cream in normal use. Furthermore, they differ from the prior art liquid lotions in that they are delivered in bar form, thereby avoiding the emulsion stability problems noted in the prior art liquid compositions. Thus, the described compositions are unique, different and represent a new concept which is not suggested by any of the prior-described compositions.

SUMMARY OF THE INVENTION

This invention relates to a non-foaming, cleansing and conditioning bar which comprises a mixture of a C-14–C-18 alkanol emollient and either a sodium or potassium saturated C-12–C-18 monocarboxylate or a water soluble, sodium or potassium, non-soap, anionic detergent selected from the group consisting of isethionate, sulfate and sulfonate detergents or a mixture of said monocarboxylate and said detergent in a weight ratio of emollient to monocarboxylate or detergent or mixture thereof above about 1.3:1 which yields a non-foaming, superfatted, cleansing and conditioning cream upon being rotated in the wetted hands of the user. Also included within the scope of the invention is a method of cleansing and conditioning the skin comprising the step of forming a cream by rotating the non-foaming, cleansing and conditioning bar in the wetted hands of the user.

More particularly, the non-foaming, cleansing and conditioning bar consists essentially of about 8% to 38% by weight of an anionic surfactant selected from the group consisting of a sodium or potassium salt of a C-12–C-18 saturated monocarboxylic acid, a water-soluble, non-soap, anionic detergent selected from the group consisting of sodium and potassium salts of C-8–C-18 acyl isethionates, C-8–C-18 alkyl sulfates, C-10–C-20 alkyl sulfonates, C-8–C-18 alkyl monoglyceride sulfates, C-8–C-16 alkylbenzene sulfonates and C-8–C-18 alkyl polyethenoxy ether sulfates containing one to twelve ethenoxy groups in the molecule and mixtures thereof and mixtures of said monocarboxylic acid salt and said detergent in a weight ratio of said mono-carboxylic acid salt to said detergent of 18:1 to about 2.5:1; about 12% to 72% by weight of a water-insoluble emollient selected from the group consisting of a C-14–C-18 alkanol and mixtures of said alkanol with a C-14–C-18 alkanoic acid wherein the weight ratio of said alkanol to alkanoic acid is in the range of about 23:1 to about 0.6:1; the weight ratio of said emollient to said surfactant being from about 10:1 to about 1.3:1; 0% to 60% of a starch-derived filler; and 2% to 12% by weight of water; said bar having a pH in the range of 6.5 to 9.5 measured as a 1% by weight aqueous solution and yielding a satisfactory volume of a non-foaming, cleansing and conditioning cream of moderate viscosity when the wetted bar is rotated and manipulated between the wetted hands of the user.

In its preferred aspects the non-foaming, cleansing and conditioning bar employs a mixture of commercial cetyl alcohol and commercial stearic acid as the emollient material and a mixture of potassium soap and sodium cocoyl isethionate as the surfactant material, with the weight ratio of cetyl alcohol to stearic acid being in the range of about 5:1 to 1:1 and the weight ratio of potassium soap to sodium cocoyl isethionate is in the range of about 9:1 to 2.5:1. In its most preferred aspect, the inventive bar contains, by weight, either about 7% to 20% of dextrin or about 18% to 50% of glucose polymers as an added filler material.

In its broadest aspect, the inventive method relates to a method of cleansing and conditioning the skin comprising the steps of (a) forming a non-foaming, cleansing and conditioning cream of moderate viscosity by rotating or manipulating the wetted bar between the wetted hands of the user, said bar having the general composition described above; (b) applying the cleansing cream of step (a) to the skin to be cleansed and conditioned; (c) massaging said cream into the skin with the user's hands and fingers; and (d) rinsing the cream-treated skin with water. In its more preferred aspect, the cream is formed at a temperature of 27° C. to 40° C. by wetting the user's hands with water having a temperature of about 30° C. to 45° C. and rotating the wetted bar for at least about ten 360 degree revolutions between the wetted hands.

The non-foaming, cleansing and conditioning bar is believed to be a new product which is effective to be converted into a non-foaming, superfatted, aqueous, cleansing and conditioning cream by manipulation in the wetted hands of the user. The bar is convenient to use and eliminates the stability problems associated with prior art superfatted cleansing creams and lotions. In addition, it delivers a high proportion of emollient material in the form of a skin cleansing-conditioning cream and it does so at a low cost because the need to use and ship the water carrier component required in creams and lotions is eliminated.

DETAILED DESCRIPTION OF THE INVENTION

The essential water-immiscible emollient component of the inventive compositions is selected from the group consisting of a C-14–C-18 alkanol and mixtures of said alkanol with a C-14–C-18 saturated monocarboxylic acid wherein the weight ratio of said alkanol to said monocarboxylic acid is in the range of about 23:1 to about 0.6:1, preferrably from 5:1 to 1:1. The individual ingredients are water-insoluble, waxy and non-reactive with one another. They provide desirable lubricating benefits to skin in the presence of soap and have been employed as emollients in soap bars for mnay years.

Suitable C-14–C-18 alkanol emollients include myristyl alcohol, cetyl alcohol, stearyl alcohol and mixtures thereof. The individual alkanols are found in nature as a component of fats and oils, but also can be prepared by chemical synthesis. For example each of cetyl alcohol (1-hexadecanol) and stearyl alcohol (1-octadecanol) is a component of the sperm oil found in the head and vertebrae of the sperm whale. In addition each can be obtained by catalytic reduction of fats containing palmitic acid and stearic acid, but such process yields mixtures of alkanols rather than the pure individual alkanols. Preferred alkanol emollients are C-16–C-18 alkanols such as cetyl alcohol and mixtures of cetyl and stearyl alcohol. Pure cetyl alcohol is a white, crystalline solid which is insoluble in water and soluble in alcohol.

Other suitable compounds which may be used in admixture with the C-14–C-18 alkanol include myristic acid, palmitic acid, stearic acid and mixtures of said acids. C-14–C-18 saturated monocarboxylic acids are found in naturally occurring fats and oils. For example, stearic acid comprises 20% to 30% by weight of animal fats and about 34% by weight of cocoa butter. Saturated C-14–C-18 monocarboxylic acids of high purity may be obtained by hydrolysis of hydrogenated oils and distillation of the resultant mixture of fatty acids. However, since it is not possible to separate saturated fatty acids from unsaturated fatty acids by distillation, the commercial C-14–C-18 saturated monocarboxylic acids can contain minor amounts of other fatty acids, including unsaturated C-14–C-18 monocarboxylic acids. A preferred emollient component is a mixture of cetyl alcohol and stearic acid wherein the weight ratio of cetyl alcohol to stearic acid is in the range of about 23:1 to 0.6:1, most preferably about 5:1 to 1:1.

The proportion of the emollient component in the finished bar generally will be from about 12% to about 72%, preferably about 19% to about 60%, by weight.

The essential anionic surfactant component of the inventive bars is selected from the group consisting of sodium and potassium salts of C-12–C-18 saturated monocarboxylic acids, a water-soluble, non-soap, anionic detergent selected from the group consisting of sodium or potassium salts of C-8–C-18 acyl isethionates, C-8–C-18 alkyl sulfates, C-10–C-20 alkyl sulfonates, C-8–C-18 monoglyceride sulfonates C-8–C-16 alkylbenzene sulfonates and C-8–C-18 alkyl polyethenoxy ether sulfates containing one to twelve ethenoxy groups in the molecule and mixtures thereof and mixtures of said monocarboxylic acid salt with said non-soap detergent in specified ratios. Suitable saturated monocarboxylic acids which may be neutralized to form the sodium or potassium salt include lauric acid, myristic acid, palmitic acid, pentadecanoic acid, heptadecanoic acid, stearic acid and mixtures thereof. The acids containing an even number of carbon atoms can be obtained by hydrolysis of hydrogenated natural fats or oils, e.g., coconut oil, palm kernel oil and beef tallow, as well as from synthetic sources; whereas the acids containing an odd number of carbon atoms are available from synthetic sources. The sodium and potassium salts of the saturated monocarboxylic acids are obtained by neutralizing the monocarboxylic acid with an alkaline sodium or potassium salt such as sodium hydroxide, potassium hydroxide, potassium carbonate or sodium carbonate in a known manner. As mentioned in the discussion of C-14–C-18 saturated monocarboxylic acids above, it is difficult to obtain individual acids of high purity, and therefore, the commercial saturated C-12–C-18 monocarboxylic acid usually contains minor proportions of other saturated and unsaturated C-12–C-18 carboxylic acids. For example, one commercial potassium stearate is a salt of a mixture of 65% stearic acid, 30% palmitic acid, 3% myristic acid and 1% oleic acid and another commercial potassium stearate contains by weight, 45% of potassium stearate and 55% potassium palmitate. The preferred monocarboxylate salts are the potassium salts and such preferred potassium salts include commercial potassium stearate, commercial potassium palmitate and potassium salts of commercial mixtures of palmitic acid and stearic acid, with the commercial potassium stearate containing 65% by weight of potassium stearate being most preferred.

As an alternate to the sodium and potassium salts of C-12–C-18 saturated monocarboxylic acids, the anionic surfactant component may be a water-soluble, non-soap, anionic sodium or potassium salt of a C-8–C-18 alkyl sulfate or alkyl (polyethenoxy) ether sulfate, a C-10–C-16 alkylbenzene sulfonate, a C-10–C-20 alkyl sulfonate, a C-8–C-18 alkyl monoglyceride sulfate or a C-8–C-18 acyl isethionate. Suitable alkyl sulfates include sodium lauryl sulfate, potassium myristyl sulfate and sodium C-10–C-16 alkyl polyethenoxy sulfates containing from 1–12 ethenoxy groups in the molecule. Satisfactory alkylbenzene sulfonates may contain either a branched chain or straight chain alkyl group, with the straight chain alkyl being preferred for biodegradability, and suitable alkylbenzene sulfonates include sodium dodecylbenzene sulfonate, potassium dodecylbenzene sulfonate, sodium decylbenzene and sodium pentadecylbenzene sulfonate. Suitable alkane sulfonates include sodium C-13–C-17 alkane sulfonate, sodium tetradecyl sulfonate and sodium pentadecyl sulfonate. Among the suitable C-8–C-18 alkyl monoglyceride sulfates are the sodium and potassium salts wherein the alkyl portion is derived from coconut oil, e.g., sodium coconut monoglyceride sulfate. Satisfactory acyl isethionates correspond to the formula RCOOCH2CH2SO3M wherein the RCO is an acyl radical of 8 to 18 carbon atoms and M is sodium or potassium. Satisfactory materials include the salts of the fatty acid mixture derived from coconut oil in which a major proportion of C-12 and C-14 fatty acids are present. Preferred non-soap detergents are the alkyl ethenoxy sulfates, monoglyceride sulfates and acyl isethionates, with said isethionates being most preferred. This is surprising in view of the fact that isethionates are widely recognized foaming agents in soap bar compositions and that a substantially non-foaming composition is desired herein.

In addition, the anionic surfactant component may be a mixture of the foregoing sodium and potassium salts of C-12–C-18 saturated monocarboxylic acids with said non-soap anionic detergent salt in a weight ratio of soap to anionic non-soap detergent of about 18:1 to about 2.5:1, preferably 9:1 to about 2.5:1, most preferably about 5:1. It is preferred that the surfactant component in the inventive bars be a mixture of the preferred potassium soap and a water-soluble, non-soap, anionic detergent. As stated in the preceding paragraph, the most preferred anionic detergent is the sodium C-8–C-18 acyl isethionate containing a major proportion of C-12–C-14 acyls in the acyl group.

The proportion of the anionic surfactant material in the final bar composition will be from about 8% to 38%, preferably about 12% to 35%, by weight.

An important aspect of the inventive, non-foaming, mild, cleansing bars is the weight ratio of the emollient material to the anionic surfactant material. Generally, such weight ratio will be about 10:1 to about 1.3:1, preferably about 4:1 to about 1.5:1. Typically, when the ratio is less than the minimum ratio of about 1.3:1, the cleansing bars produce a significant volume of foam and/or a liquid cream of low viscosity, neither characteristic being desirable. On the other hand, a weight ratio higher than the maximum of about 10:1 results in a bar which is essentially insoluble and upon use produces a limited volume of a low viscosity liquid in the evaluation test hereinafter described.

The remaining essential ingredient in the described cleansing bars is water. In general, the proportion of water is from 2% to 12%, preferably about 6% to 11%, by weight of the finished bar. Water functions as a plasticizer in the described bars. Too much water may result in bars which are sticky and difficult to process or, alternatively are too soft. Because the proportion of water has a significant effect on processing, particularly plodding, the proportion of water must be correlated with the processing conditions.

While the foregoing essential components result in bars which form a relatively viscous, non-foaming, cleansing cream in use which is effective to cleanse and lubricate the skin without significantly adversely affecting the acid mantle of the skin, it has been noted that preferred bars include certain optional materials. For example, the presence of either 1% to 8%, preferably 3% to 6%, by weight of titanium dioxide or 3% to 15%, preferably 6% to 12%, by weight of zinc oxide yields a bar—and the cream generated in the hand—with a bright white color.

Another optional component which desirably is present is a starch-derived filler selected from the group consisting of dextrin, powdered pregelatinized starch, non-gelling amylopectin starch and glucose polymers in amounts selected from the range of about 4% to about 60% by weight. The proportion of the starch-derived filler varies with the particular filler selected because the aforementioned fillers vary in molecular weight, water solubility and viscosity, and these properties in turn cause variations in the physical characteristics of the resultant bars. Generally, smaller amounts of the high molecular weight and more viscous starch-derived filler, e.g., powdered pregelatinized starch, and larger amounts of the lower molecular weight and low viscosity starch-derived filler, e.g., glucose polymers will be employed.

Dextrin is an intermediate product formed either by acid or enzyme catalyzed hydrolysis of starch or by dry heating of unmodified starch which is characterized by a lower moisture content, a decreased solution viscosity and an increased solubility in cold water than the original starch. Generally, the solubility of dextrin in water at a temperature of about 22° C. will range from 25% to 85%, preferably 25% to 55%, by weight and its moisture content is from about 4% to 10% by weight. Commercially, a white dextrin product may be produced by spraying dried starch with hydrochloric acid, drying to a moisture content of 1% to 5% moisture and hydrolyzing at a temperature of 95° C. to 120° C. A particularly preferred dextrin may be purchased under the tradename Amaizo 1104 Dextrin. When employed, the proportion of dextrin will be from 4% to 25%, preferably from 7% to 20%, by weight of the final bar.

Powdered pregelatinized, gelling starch and powdered, non-gelling amylopectin starch also may be employed as the starch-derived filler ingredient. Each of these materials is obtained by treating the starch granules obtained from corn, wheat or potatoes. Such treatment generally improves the solubility of the starch granules in water having a temperature of about 22° C. If powdered starch is present as the starch-derived filler, its proportion generally will be about 4% to 15%, preferably 5% to 10%, by weight of the resultant bar.

Glucose polymers obtained by acid and/or enzyme catalyzed, partial hydrolysis of starch are a preferred filler material. Glucose polymers are characterized by a relatively low molecular weight of about 1600–2200, a high solubility in water and a low viscosity, e.g., 200–300 cps. for a 50% concentration in water at 28° C. as measured on a Brookfield Viscometer using a #2 spindle. Further, the viscosity of aqueous solutions is Newtonian. Glucose polymers may be produced by acid and/or enzyme catalyzed hydrolysis of gelatinized starch solutions, preferably cornstarch solutions, for a period of time sufficient to yield a starch sirup of polymers of the desired molecular weight. The resultant product is sold in the form of a powder having a moisture content of 6% maximum. A particularly preferred glucose polymer may be purchased under the tradename MALTRIN® M-100. This preferred glucose polymer is water soluble and has a molecular weight of about 1800, with about 36% by weight thereof having a degree of polymerization less than 10. Glucose polymers are the preferred filler because they are low in cost and can be employed in large amounts, i.e., generally from 10% to 60%, preferably from 18% to 50%, by weight. Because of the high water solubility and low viscosity of glucose polymer solutions, bars containing 40% by weight of glucose polymers—MALTRIN® M100—are cohesive, exhibit a smooth feel and desirable slip and produce a highly homogeneous cream. Surprisingly, the resultant bars represent an optimum when evaluated according to the tests set forth herein.

Inclusion of a filler enables the formulator to reduce the cost of the ultimate bar and to improve the processability of the bar. More specifically, improved processibility is manifested by reducing the energy requirements needed for mixing and extrusion of the bars. Furthermore, by judicious selection of said filler, the properties of the final bar, e.g., wear rate, slip and smoothness, can be controlled. Also, use of dextrin having a solubility of 25% to 55% by weight in cool water provides a desirable wear rate because of its water-insoluble content; and use of non-gelling amylopectin starch or gelling, pregelatinized starch helps to provide good slip-feel properties. Furthermore, low cost bars having optimal cream volume and consistency properties are obtained when 18% to 50% by weight of glucose polymers are present.

A further optional ingredient which desirably may be present in the preferred inventive bars is a conventional liquid cosmetic emollient. Such material appears to modify the skin feel characteristics of the emollient film left on the skin of the user. Suitable cosmetic, liquid emollients such as C-12–C-15 alcohols benzoate, isopropyl myristate, mineral oils, lanolin and lanolin derivatives and triglycerides such as coconut oil desirably can be included in the preferred bars in amounts of 1% to 5%, preferably 2% to 4%, by weight of the finished bar. Preferred liquid emollients are isopropyl myristate and mineral oil.

Finally, the bar compositions can contain any of the usual optional ingredients commonly found in soap bars and cleansing lotions to modify the color, odor or antibacterial properties. For example, perfumes generally will be present in proportion of about 0.1% to 2% by weight. If colored bars are desired, dyes or pigments may be present in concentrations from about 0.001% to 0.5% by weight.

Usually, preservatives such as formaldehyde or a Paraben® or Kathon CG® may be present, too. Similarly, where antimicrobial properties are desired, an antimicrobial, e.g., 3, 4, 5 tribromosalicylanilide, 3, 4, 4 trichlorocarbanilide, etc., may be included in amounts of 0.2% to about 2% by weight. Furthermore, polymers such as Carbopols® 720 and 934 may be included in amounts up to about 2% by weight. Small amounts, e.g., 0.5% to 5%, of urea or polyethylene glycols sold under the tradename Carbowax also may be present. In addition, from 1% to 4% by weight of potassium or sodium isethionate may be included to improve the processing characteristics of the bar.

Bars of this invention may be made in any suitable manner by well known techniques used for manufacturing superfatted soap and synthetic detergent-soap bars. Preferably, the C-14–C-18 alkanol, the optional stearic acid, potassium stearate and the optional, supplemental anionic surfactant are placed into a stainless steel mixing vessel and heated to a temperature of from 75° C. to 90° C. Thereafter, the water is added and the resultant mixture is mixed with a homogenizer mixer and agitation continues as the temperature is reduced to about 75° C., at which time titanium dioxide and perfume, if present, are added with continued agitation. The resultant mixture is solidified by cooling to a temperature of from 22° C. to 43° C. either by pouring the molten liquid into trays or by passing said liquid over chilled rolls. Then the chilled material in subdivided form is passed through a plodder and the resultant extruded billet is cut and stamped into bars. Preferably, the particulate material first is fed to a preplodder from which it is extruded in the form of ⅜" to ½" pellets and these pellets are fed into the final plodder from which the composition is extruded as a billet or log at a temperature of from 30° C. to 40° C.

When the optional filler ingredient is present in the finished bar, this ingredient usually is mixed with the added water and heated to a temperature of 70° C. to 90° C. with agitation. This mixture is then slowly added to the molten mixture of emollient material and surfactant material while it is being agitated by the homogenizer mixer at a temperature of from 75° C. to 90° C. Again, the resultant mixture may be solidified either by pouring into aluminum trays and allowing it to cool to about 27° C. to 40° C. or by pouring it onto a chilled roll mill where it is removed in flake form.

It should be recognized that the foregoing process can be modified to form the mixture of sodium or potassium stearate and stearic acid when present in situ simply by neutralizing stearic acid with aqueous sodium or potassium hydroxide at a temperature of 75° C. to 90° C. to a pH in the range of 6 to 9.5 and thereafter adding C-14–C-18 alkanol and, optionally, an anionic surfactant to this mixture.

Generally, the pH of the inventive compositions as measured by a 1% weight concentration of the finished bar composition in 23° C. water ranges from about 6 to 9.5, preferably from 6.5 to 9.0. pH is controlled by adding controlled amounts of a compatible acid, e.g., citric acid, or alkali, e.g., sodium or potassium hydroxide, prior to the step of cooling the composition in the above-described process. At the described pH, the inventive bars are essentially neutral and deleterious effects on the skin of the user due to pH are minimized.

When the inventive bar is used for personal washing, it is rotated between the wetted hands of the user until they are coated with a cleansing cream. The nature of the cream is assessed by the user subjectively based in part upon the volume of cream formed and the consistency or viscosity of the cream. Additionally, other factors such as creaminess, skin feel after rinsing, etc., remain which cannot be determined by physical measurement, but which only can be determined by panels of trained users. However, the cream obtained from the inventive bars is effective in removing particulate soil and oily soil from the skin and in conditioning the skin by imparting a desirable skin feel to the rinsed and dried hands. The desirable skin feel is such that the skin is smooth, soft or supple and has a lubricated, non-oily surface. Such skin feel is unlike the external skin feel which accompanies either the use of soap or which accompanies the use of well known foaming superfatted detergent-soap bars described in U.S. Pat. No. 3,376,229 for example.

While the reasons for the improved skin feel are not readily apparent because many of the same individual ingredients found in the prior art bars are employed—but in different proportions—, it is postulated that the improved skin feel is due principally to the absence of foam and to the higher weight ratio of emollient material to surfactant material in the inventive bars. Furthermore, at the lower concentration of surfactant material, it is believed that the continuous phase of the liquid cleansing cream which is formed enables oily soil to be removed from the skin without substantial defatting of the cleansed skin while at the same time permitting deposition of additional superfatting or emollient ingredients from the cream onto the skin. It is submitted that the latter condition has not been attained by the prior art superfatted bars which are characterized by foam and an excess of surfactant concentration as compared to the concentration of the emollient material present. Also, the reduced concentration of surfactant minimizes dehydration of the skin by the surfactant ingredient and the resultant "dryness" associated therewith even though soap is present. Furthermore, it is believed that the effects of the inventive bars have not been attained by the prior art cleansing lotions because they are characterized by different compositions at the point of use.

Although the inventive bars tend to form skin creams in use, the compositions in bar form have the appearance, feel and processing characteristics of soap bars. More particularly, the bar surface is uniform, has a desirable feel and is not greasy or sticky. In addition, the bar maintains its shape and hardness under conditions of normal use and storage. Also, it does not develop significant surface cracks or sloughing in use and its solubility in water and wear rate is about equal to or better than soap or superfatted detergent bars. Finally, these inventive bars can be processed in conventional equipment used for making soap bars.

The characteristics of the cleansing cream formed by using the inventive bars are defined using a Cream Consistency Test. In this test, a bar is used by the user to generate a moderately viscous cream using water of standard hardness at a standard temperature which simulates conditions of consumer use. More particularly, the bar and the user's hands are wetted with water flowing from a faucet at a temperature of about 41° C. for about five seconds and then the bar is rotated end over end (ten 360 degree revolutions) between the hands. The bar is then set down and the volume of cream generated—no foam is generated—from this process and the viscosity of said cream is observed and assigned an appropriate value from Table I below. To obtain an overall rating for the bar, the value for the volume is multiplied by the value for the viscosity. It should be noted that any bar which generates a water-thin cream, foams or fails to form an appreciable amount of cream will receive an overall rating of zero when the volume value is multiplied by the viscosity value. Any bar receiving an overall rating of two or less is not satisfactory.

TABLE I

| VOLUME | | VISCOSITY | |
|---|---|---|---|
| Value | Description | Value | Description |
| 4 | Very high | 4 | Very high |
| 3 | High | 3 | High |
| 2 | Medium | 2 | Medium |
| 1 | Low | 1 | Low |
| 0 | Virtually insoluble | 0 | Sudsy or watery |

In the foregoing test, the volume of cream generated is distributed over the palm and back of each hand. The volume of cream can be approximated by gripping the wrist of one hand with the opposite hand and squeezing as the opposite hand is moved upwardly so as to transfer the cream to between the thumb and the index finger of the opposite hand. The collected cream is placed in a beaker and the process of gripping and squeezing is repeated four additional times. Then the gripping and squeezing procedure is repeated on the opposite hand. This process is reproduceable for each operator and a panel of operators is employed to minimize operator variations. The hands are rinsed at the completion of the collection procedure.

The consistency of the generated cream or lotion can be ascertained quickly by simply holding the hands in a vertical position with the fingers pointed down immediately after the completion of the ten rotations and the setting down of the bar. If a relatively moderate viscosity liquid is obtained which flows fairly slowly downward on the vertical hand, then the viscosity is satisfactory. Finally, if the cream is so viscous that a film does not form on the vertical hand, then the cream is unsatisfactory, too. Thus, it will be understood that the desired consistency of the cream or lotion generated is similar to that of a medium viscosity cream which forms a coherent film which flows at least slowly under the force of gravity.

As indicated heretofore, the present invention also includes a method for cleansing and conditioning the skin, said method comprising the steps of (a) forming a substantially non-foaming, cleansing cream of moderate viscosity by rotating and manipulating a wetted bar between the wetted hands of the user, said bar having the general composition set forth in the Summary of the Invention; (b) applying the cleansing cream of step (a) to the skin to be cleansed and conditioned; (c) massaging said cream into the skin with the user's hands and fingers; and (d) rinsing the cream-treated skin with water. Preferably, the step of forming the cream yields a cream having a temperature in the range of about 27° C. to 40° C. by wetting the hands and the bar with water having a temperature in the range of 30° C. to about 45° C., i.e., warm to hot tap water, and the cream is formed by rotating the bar end to end for at least about ten 360 degree revolutions. The solids content of the cream formed by this process ranges from about 2.5% to about 12%, preferably 4% to 7%, by weight based upon the quantitative observations that each of the wetted hands retains four grams of water and the wetted bar retains about one gram of water and from ¼ to 1 gram of the bar composition is removed when the bar is rotated from ten to twenty-five 360 degree revolutions.

The invention is further illustrated by the examples which follow. Unless otherwise stated, the proportions in the examples and elsewhere in the specification are in percent by weight. Furthermore, the examples are illustrative of the described invention, but do not limit it.

EXAMPLE 1

| Ingredient | % by wt. |
|---|---|
| Potassium stearate* | 28.0 |
| Sodium C-8–C-18 acyl isethionate** | 4.0 |
| Cetyl alcohol | 26.0 |
| Stearic acid | 26.0 |
| Titanium dioxide | 5.0 |
| Perfume | 1.0 |
| Water, salts | q.s. |
| Total | 100.0 |

*Contains, by weight, 65% potassium stearate, 35% potassium palmitate, 3% potassium myristate, 1% potassium oleate and 1% water.

**Purchased from GAF Chemicals Corporation under the tradename Igepon AC 78 Surfactant which contains, by weight, 2% water, 84–92% of sodium acyl isethionate and 5%–10% of free fatty material.

This bar is prepared by adding the potassium stearate, sodium acyl isethionate, stearic acid and cetyl alcohol to a mixing vessel in which these ingredients are melted by heating to about 80° C. Next, the balance of the water is added at a temperature of about 75° C. and this mixture is added to the molten mixture while it is being agitated with a homogenizer mixer. The resultant mixture is agitated at a temperature of about 85° C. for about fifteen minutes. Thereafter, the heated mixture is reduced in temperature to about 75° C., at which point the titanium dioxide and perfume are added in the presence of continuing agitation. Then, the heated composition is discharged into aluminum foil trays where it cools to about room temperature (25° C.). The solidified mixture is broken into pieces and is extruded twice through a soap plodder. The first pass through the plodder reduces the material to cylindrical pellets having a diameter of about 1 cm. and a length of about 1.25 cm. During the second pass, the material is extruded as a log having an eliptical cross section which is severed into 7.6 cm. sections which are pressed into bars. The resultant bars have a bright white color and a smooth surface appearance which is free of cracks at the extrusion temperature of 35° C. The finished bars contain 6% by weight of free water (based upon moisture loss at 105° C.) and an aqueous solution containing 1% by weight of the composition exhibits a pH of 9.

When the bar of Example 1 was evaluated by female users against their favorite brand of skin cleansing and conditioning composition, the results indicated most women preferred the inventive cleansing cream bar over their favorite Ivory® or Dove® or Ponds® Cold Cream composition.

Satisfactory bars also are achieved using an alternative process wherein the molten mixture is fed to a chilled 3-roll mill prior to the addition of the titanium dioxide and perfume where it is cooled to about 39° C. and formed into ribbons or flakes. These flakes are then mixed with the titanium dioxide and perfume in a standard soap amalgamator apparatus and this mixture is passed to a 3-roll mill to form flakes which are fed to a vacuum soap plodder to form an extruded billet which is cut and stamped into bar form in the same manner described above.

EXAMPLES 2–10

The following compositions indicate the importance of the weight ratio of the emollient material to the surfactant material in achieving the desired cream in the evaluation test used to evaluate cream volume, cream viscosity and cream sudsing characteristics. Examples 2, 3 and 7—9 describe bars falling within the scope of the invention and Examples 4–6 and 10 describe comparative bars which are outside the scope of the claimed invention.

| | % by weight | | | |
|---|---|---|---|---|
| Ingredient | Ex. 2 | Ex. 3 | Ex. 4 | Ex. 5 |
| Cetyl alcohol | 72 | 54 | 36 | 18 |
| Potassium stearate* | 18 | 36 | 54 | 72 |
| Water, salt | 10 | 10 | 10 | 10 |
| Total | 100 | 100 | 100 | 100 |
| Emollient/Surfactant Weight Ratio | 4:1 | 1,5:1 | 0.67:1 | 0.25:1 |
| Overall Rating | 4 | 6 | 0 | 0 |

| Ingredient | Ex. 6 | Ex. 7 | Ex. 8 | Ex. 9 | Ex. 10 |
|---|---|---|---|---|---|
| Cetyl alcohol | 85.5 | 81 | 72 | 54 | 36 |
| Sodium C-8–C-18 acyl isethionate** | 4.5 | 9 | 18 | 36 | 54 |
| Water, salt | 10.0 | 10 | 10 | 10 | 10 |
| Total | 100.0 | 100 | 100 | 100 | 100 |
| Emollient/Surfactant Weight Ratio | 19:1 | 9:1 | 4:1 | 1.5:1 | 0.67:1 |
| Overall Rating | 1 | 4 | 9 | 2 | 0 |

The foregoing examples clearly show that bars having a ratio of emollient to anionic surfactant—whether soap or non-soap anionic detergent—outside the range of 10:1 to 1.3:1 are unsatisfactory.

EXAMPLES 11-14

These compositions which follow also illustrate the importance of the weight ratio of emollient material to surfactant material in the inventive compositions and further demonstrate the advantage of using a mixture of potassium stearate and a second anionic detergent—sodium cocoyl isethionate—as the surfactant material. Examples 11 and 12 describe compositions within the scope of the invention and Examples 13 and 14 are comparatives. The overall ratings of the resultant bars in the Cream Consistency Test are provided as in Examples 2-10.

| | % by weight | | | |
|---|---|---|---|---|
| Ingredient | Ex. 11 | Ex. 12 | Ex. 13 | Ex. 14 |
| Cetyl alcohol | 68.8 | 51.6 | 32.4 | 17.2 |
| Potassium stearate* | 17.2 | 32.4 | 51.6 | 68.8 |
| Sodium cocoyl isethionate** | 4.0 | 4.0 | 4.0 | 4.0 |
| Water, salt | 10.0 | 12.0 | 12.0 | 10.0 |
| Total | 100.0 | 100.0 | 100.0 | 100.0 |
| Emollient/Surfactant Weight Ratio | 3.2:1 | 1.4:1 | 0.6:1 | 0.24:1 |
| Overall Rating | 6 | 9 | 0 | 0 |

Similar satisfactory bars are obtained when 4% by weight of either sodium C-12–C-15 alkyl triethenoxy ether sulfate or sodium C-10–C-14 alkylbenzene sulfonate is substituted for the sodium cocoyl isethionate in the compositions of Examples 11 and 12.

EXAMPLES 15 and 16

Formulations which yield bars with preferred overall evaluation test results are described in the following examples.

| | % by weight | |
|---|---|---|
| Ingredient | Ex. 15 | Ex. 16 |
| Cetyl alcohol | 45.6 | 42.6 |
| Stearic acid | 10.0 | 10.0 |
| Potassium stearate* | 30.4 | 28.4 |
| Sodium cocoyl isethionate** | 4.0 | 4.0 |
| Titanium dioxide | — | 5.0 |
| Water, salt | 10.0 | 10.0 |
| Total | 100.0 | 100.0 |
| Emollient/Surfactant Weight Ratio | 1.6:1 | 1.6:1 |
| Overall Rating | 6 | 6 |

Each of the resultant bars contains a mixture of cetyl alcohol and stearic acid as the emollient material and this mixture provides a desirable high viscosity—a 3 rating—in the Cream Consistency Test. Furthermore, the bar of Example 16 has a bright white color due to the inclusion of the titanium dioxide therein.

EXAMPLE 17

A highly preferred, cost effective composition in accordance with this invention follows:

| Ingredient | % by weight |
|---|---|
| Potassium stearate* | 21.1 |
| Sodium C-8–C-18 acyl isethionate** | 3.1 |
| Cetyl alcohol | 30.0 |
| Stearic acid | 10.0 |
| Zinc oxide | 10.0 |
| Dextrin*** | 18.0 |
| Perfume | 1.0 |
| Water, salts | 6.8 |
| Total | 100.0 |

***Dextrin has a water solubility in water at 22° C. in the range of 25% to 55% by weight and is purchased from American Maize Products Company under the tradename Dextrin 1104

The resultant bar is white, has a smooth surface which is free of cracks and costs less than the bar of Example 1 due to the inclusion of dextrin as a filler or extender. In order to compensate for the water-solubility of part of the dextrin, the proportion of the water-soluble detergent—the mixture of potassium soap and the sodium acyl isethionate—is reduced by about 10% by weight. Furthermore, when a dextrin having a water solubility of 60% to 85% by weight is employed, the proportion of dextrin must be reduced by about 50% to 70% by weight. Since bars containing dextrin are more prone to bacterial deterioration, a preservative such as methyl or propyl Paraben ® is included in such bars. The bar of this example achieved a very high overall rating of 12 in the Cream Consistency Test, thereby leading to its classification as a highly preferred bar.

Examples 18 and 19 illustrate the importance of the ratio of emollient to surfactant in bars containing dextrin as a filler.

EXAMPLES 18 and 19

| | % by weight | |
|---|---|---|
| Ingredient | Ex. 18 | Ex. 19 |
| Cetyl alcohol | 42.4 | 21.2 |
| Stearic acid | 10.0 | 10.0 |
| Potassium stearate* | 10.6 | 31.8 |
| Sodium cocoyl isethionate** | 4.0 | 4.0 |
| Titanium dioxide | 5.0 | 5.0 |
| Dextrin*** | 18.0 | 18.0 |
| Sodium isethionate | 2.0 | 2.0 |
| Perfume | 1.0 | 1.0 |
| Water, salt | 7.0 | 7.0 |
| Total | 100.0 | 100.0 |
| Emollient/Surfactant Weight Ratio | 3.6:1 | 0.87:1 |
| Overall Rating | 6 | 0 |

When either sodium C-8–C-18 alkyl monoglyceride sulfate or sodium C-12–C-15 alkyl polyethenoxy ether sulfate containing from 5 to 12 ethenoxy groups in the molecule is substituted for the C-8–C-1 acyl isethionate salt in the composition of Example 18 above, cleansing-conditioning bars with equivalent cleansing and conditioning properties are achieved. Similarly, satisfactory bars are achieved when about 4% to 15% by weight of a 1:1 weight mixture of particulate gelling pregellatinized starch and particulate non-gelling amylopectin starch is substituted for the 18% by weight of dextrin in the composition of Example 18 and the concentrations of emollient material and surfactant material are increased correspondingly to make up for the balance of the omitted dextrin ingredient.

Example 20 describes a low cost bar containing glucose polymers as the filler with optimal cream consistency properties.

| Ingredient | % by weight |
|---|---|
| Cetyl alcohol | 18.0 |
| Stearic acid | 6.0 |
| Potassium stearate* | 13.5 |
| Sodium cocoyl isethionate** | 2.4 |
| Zinc oxide | 8.2 |
| Glucose polymers** | 40.0 |
| Perfume | 1.0 |
| Water, salt | q.s. |
| Total | 100.0 |

***Glucose polymers purchased under the tradename MALTRIN ® M 100 having a molecular weight of about 1800 and a moisture content of 6% by weight maximum In the Cream Consistency Test the bars of Example 20 had a cream volume rating of 4 and a viscosity rating of 4 giving the bar a rating of 16.

Examples 21-24 set forth other compositions of bars containing glucose polymers as a filler.

| | % by weight | | | |
|---|---|---|---|---|
| Ingredient | Ex. 21 | Ex. 22 | Ex. 23 | Ex. 24 |
| Cetyl alcohol | 30.0 | 14.0 | 32.0 | 9.0 |
| Stearic acid | 10.0 | 5.0 | 10.0 | 3.0 |
| Potassium stearate* | 21.0 | 11.0 | 24.0 | 7.0 |
| Sodium cocoyl isethionate** | 3.0 | 1.6 | 4.3 | 1.3 |
| Zinc oxide | 8.0 | 8.0 | 8.0 | 8.0 |
| Glucose polymers**** | 18.0 | 50.0 | 10.0 | 60.0 |
| Water, perfume, salt | q.s. | q.s. | q.s. | q.s. |
| Total | 100.0 | 100.0 | 100.0 | 100.0 |

Examples 21 and 22 exemplify the range of the preferred proportions of glucose polymers as a filler and Examples 23 and 24 exemplify the range of the broad proportions of said filler.

In use, the described bars are effective to cleanse and condition the skin, particularly the hands, face and neck and leave them with a desirable soft feel as well as a desirable smooth feel after application of the composition in cream form, rinsing and drying. The skin effects produced in use are unlike those attained by the prior art bar and skin lotion compositions and thus the inventive compositions and process are surprising and unobvious from the state of knowledge in the art.

What is claimed is:

1. A non-foaming, skin cleansing-conditioning bar consisting essentially of about 8% to 38% by weight of an anionic surfactant material selected from the group consisting of a sodium or potassium salt of a C-12-C-18 saturated monocarboxylic acid, a water-soluble, non-soap, anionic detergent selected from the group consisting of sodium and potassium salts of C-8-C-18 acyl isethionates, C-8-C-18 alkyl sulfates, C-10-C-20 alkyl sulfonates, C-8-C-18 alkyl monoglyceride sulfates, C-8-C-16 alkylbenzene sulfonates and C-8-C-18 alkyl polyethenoxy ether sulfates containing one to twelve ethenoxy groups in the molecule and mixtures thereof and mixtures of said monocarboxylic acid salt and said non-soap detergent in a weight ratio of said monocarboxylic acid salt to said detergent of 18:1 to about 2.5:1; about 12% to 72% by weight of a water-insoluble emollient selected from the group consisting of a C-14-C-18 alkanol and mixtures of said alkanol with a C-14-C-18 alkanoic acid wherein the weight ratio of said ankanol to said alkanoic acid is in the range of about 23:1 to about 0.6:1; the weight ratio of said emollient material to said surfanctant material being from about 10:1 to about 1.3:1; 0% to 60% of a starch-derived filler; and 2% to 12% by weight of water; said bar having a pH in the range of 6 to 9.5 measured as a 1% by weight aqueous solution and yielding a satisfactory volume of a non-foaming, cleansing-conditioning cream of moderate viscosity when the wetted bar is rotated and manipulated between the wetted hands of the user.

2. A bar in accordance with claim 1 which includes a starch derivative selected from the group consisting of dextrin, powdered pregelatinized starch, powdered non-gelling amylopectin strach and glucose polymers in an amount selected from the range of 4% to 60% by weight.

3. A bar in accordance with claim 2 wherein said starch derivative is dextrin which is present in a proportion of from 4% to 25% by weight.

4. A bar in accordance with claim 2 wherein said starch derivative is glucose polymers which is present in a proportion of from 10% to 60% by weight.

5. A bar in accordance with claim 1 wherein the weight ratio of emollient material to surfactant material is from about 4:1 to about 1.5:1.

6. A bar in accordance with claim 1 wherein said emollient material is said mixture of said C-14-C-18 alkanol and said C-14-C-18 alkanoic acid.

7. A bar in accordance with claim 6 wherein said alkanol is commercial cetyl alcohol and said alkanoic acid is commercial stearic acid.

8. A bar in accordance with claim 1 wherein said surfactant material is said mixture of the potassium salt of a C-12-C-18 monocarboxylic acid and said water-soluble, non-soap, anionic surfactant.

9. A bar in accordance with claim 8 wherein said monocarboxylic acid salt contains 16 to 18 carbon atoms and said water-soluble, non-soap, anionic detergent salt is selected from the group consisting of C-8-C-18 acyl isethionates, C-8-C-18 alkyl polyethenoxy ether sulfates containing from 5 to 12 ethenoxy groups in the molecule and C-8-C-18 alkyl monoglyceride sulfates.

10. A bar in accordance with claim 9 wherein said detergent is said salt of C-8-C-18 acyl isethionate.

11. A bar in accordance with claim 9 wherein said potassium monocarboxylic acid salt is commercial potassium stearate.

12. A bar in accordance with claim 6 wherein the weight ratio of emollient to surfactant is in the range of about 4:1 to about 1.5:1.

13. A bar in accordance with claim 6 wherein said surfactant material is said mixture of the potassium salt of C-12-C-18 monocarboxylic acid and said water-soluble, non-soap, anionic detergent salt, and the weight ratio of emollient material to surfactant material is from about 4:1 to about 1.5:1.

14. A bar in accordance with claim 13 which includes said starch-derived filler in an amount selected from the range of from 4% to 60% by weight.

15. A bar in accordance with claim 14 wherein said starch-derived filler is dextrin which is present in an amount of 7% to 20% by weight.

16. A bar in accordance with claim 14 wherein said starch-derived filler is glucose polymers which is present in an amount of 18% to 50% by weight.

17. A bar in accordance with claim 2 which includes, in addition, 1% to 8% by weight of titanium dioxide.

18. A bar in accordance with claim 2 which includes, in addition, 3% to 15% by weight of zinc oxide.

19. A bar in accordance with claim 6 which includes, in addition, 1% to 5% by weight of a liquid emollient material.

20. A bar in accordance with claim 19 wherein said liquid emollient is mineral oil, said alkanoic acid is stearic acid and said anionic surfactant is a mixture of potassium stearate and C-8–C-18 acyl isethionate.

21. A bar in accordance with claim 4 wherein said anionic surfactant is a mixture of potassium stearate and sodium C-8–C-18 acyl isethionate, said emollient is a mixture of cetyl alcohol and stearic acid in a weight ratio of cetyl alcohol to stearic acid of about 5:1 to 1:1, the weight ratio of emollient to anionic surfactant is from about 4:1 to about 1.5:1 and the bar includes, in addition, 3% to 15% by weight of zinc oxide.

22. A bar in accordance with claim 21 wherein the amount of glucose polymers is 18% to 50% by weight, the amount of emollient is 19% to 60% by weight, the amount of anionic surfactant is 12% to 35% by weight and the amount of zinc oxide is 6% to 12% by weight.

23. A bar in accordance with claim 4 wherein said anionic surfactant is said sodium C-8–C-18 acyl isethionate, said emollient is a mixture of cetyl alcohol and stearic acid in a weight ratio of cetyl alcohol to stearic acid of about 5:1 to 1:1, the weight ratio of emollient to anionic surfactant is from about 4:1 to about 1.5:1 and the bar includes, in addition, 6% to 12% zinc oxide.

24. A method of cleansing and conditioning the skin comprising the steps of (a) forming a non-foaming, cleansing-conditioning cream by rotating and manipulating a wetted bar between the wetted hands of the user, said bar having the composition set forth in claim 1; (b) applying the cleansing-conditioning cream of step (a) to the skin to be cleansed and conditioned; (c) massaging said cream into the skin with the user's hands and fingers; and (d) rinsing the cream-treated skin with water.

25. A method in accordance with claim 24 wherein step (b) is carried out by applying said cream to wetted skin.

26. A method in accordance with claim 24 wherein the cream in step (a) is formed at a temperature of 27° C. to 41° C. by wetting the bar and the user's hands with water having a temperature in the range of 30° C. to 45° C. and said cream is formed by rotating said bar end over end for at least about ten 360 degree revolutions.

27. A method in accordance with claim 24 wherein said bar has the composition of claim 22.

* * * * *